(12) United States Patent
Nishiguchi et al.

(10) Patent No.: US 9,867,374 B2
(45) Date of Patent: Jan. 16, 2018

(54) FLY ATTRACTANT COMPOSITION AND FLY ATTRACTING METHOD, AS WELL AS FLY EXPELLANT COMPOSITION AND FLY EXPELLING METHOD

(75) Inventors: Naonobu Nishiguchi, Takarazuka (JP); Hiroyuki Kawano, Osaka (JP); Kazuhide Nakada, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 397 days.

(21) Appl. No.: 12/978,825

(22) Filed: Dec. 27, 2010

(65) Prior Publication Data

US 2011/0158934 A1 Jun. 30, 2011

(30) Foreign Application Priority Data

Dec. 28, 2009 (JP) ................. 2009-297955

(51) Int. Cl.
*A01N 41/04* (2006.01)
*A01N 51/00* (2006.01)
*A01N 25/00* (2006.01)
*A01N 61/00* (2006.01)

(52) U.S. Cl.
CPC ........... *A01N 51/00* (2013.01); *A01N 25/006* (2013.01); *A01N 61/00* (2013.01)

(58) Field of Classification Search
CPC ....... A01N 25/006; A01N 51/00; A01N 61/00
USPC .............................. 424/84; 514/22; 530/500
See application file for complete search history.

(56) References Cited

U.S. PATENT DOCUMENTS

| | | | |
|---|---|---|---|
| 3,223,698 A * | 12/1965 | Motoyoshi et al. .......... | 530/503 |
| 4,122,165 A | 10/1978 | Kinzer et al. | |
| 4,855,133 A | 8/1989 | Kamei et al. | |
| 6,090,415 A | 7/2000 | Stadler et al. | |
| 2001/0046986 A1 | 11/2001 | Miura et al. | |
| 2007/0071784 A1 | 3/2007 | Rakoczi et al. | |
| 2008/0089857 A1 | 4/2008 | Huchet et al. | |
| 2010/0291022 A1 | 11/2010 | Huchet et al. | |

FOREIGN PATENT DOCUMENTS

| CN | 86108161 | 6/1988 |
|---|---|---|
| CN | 201234517 | 5/2009 |
| GB | 2 067 406 | 7/1981 |
| JP | 62-026208 | 2/1987 |
| JP | 62-042903 | 2/1987 |
| JP | 5-60441 | 9/1993 |
| JP | 2003-055125 | 2/2003 |
| JP | 2003-321303 | 11/2003 |
| JP | 2008-143804 | 6/2006 |
| JP | 2007-500159 | 1/2007 |
| JP | 2008-519836 | 6/2008 |
| JP | 4324308 | 6/2009 |
| WO | 2007/081695 | 7/2007 |
| WO | 2008/012756 | 1/2008 |
| WO | WO 2008/055882 | * 5/2008 |

OTHER PUBLICATIONS

Tanio et al—abstract # 149:71928 HCAPLUS—of JP 2008143804—Jun. 26, 2008 Use of Guanidine Comound for Contorl of Flies.*
Nakada K et al., English Abstract of JP 2008143804 A from East, publishe4d Jun. 26, 2008.*
Valent, Title: Arena® 0.25 G insecticide; Material safety data sheet, revised version available Jan. 22, 2009.*
Office Action dated Feb. 18, 2014 in corresponding European Application No. 10 197 115.8.
Extended European Search Report dated May 22, 2013 in counterpart European Patent Application No. 10197115.8.
Chinese Office Action, with English translation, dated Jun. 9, 2013 in Chinese Patent Application No. 201010609007.5.
"Ligonosite® 458 Sodium Lignosulfonate Powder", Jan. 1, 2000, pp. 1-4, XP55062421, Retrieved from Internet: URL: http://www.hillbrothers.com/msds/pdf/n/lignosite-458-dry.pdf.
Japanese Office Action dated Aug. 6, 2014 issued in counterpart Japanese Patent Application No. 2010-283494 with English Translation.
Australian Office Action dated Nov. 4, 2014 issued in counterpart Australia Patent Application No. 2010257448.
Taiwanese Office Action dated Mar. 13, 2015 issued in counterpart Taiwanese Patent Application No. 99145433. (with English translation).
Korean Office Action dated Oct. 17, 2016 issued in Korean Patent Application No. 2010-0133592 (with English translation).
Brazilian Office Action dated Dec. 27, 2016 issued in Brazilian Counterpart Patent Application No. PI 1004973-8 (with English Translation).
Substantive Examination Adverse Report dated Aug. 15, 2017 in Malaysian Application No. PI 2010006150.

* cited by examiner

*Primary Examiner* — Yanzhi Zhang
(74) *Attorney, Agent, or Firm* — Wenderoth, Lind & Ponack, L.L.P.

(57) ABSTRACT

Provided are a fly attractant composition containing a ligninsulfonate as an active ingredient, and a fly expellant composition containing 5 to 20% by weight of a ligninsulfonate and at least 0.1% by weight but less than 5% by weight of an insecticidal active ingredient.

4 Claims, 1 Drawing Sheet

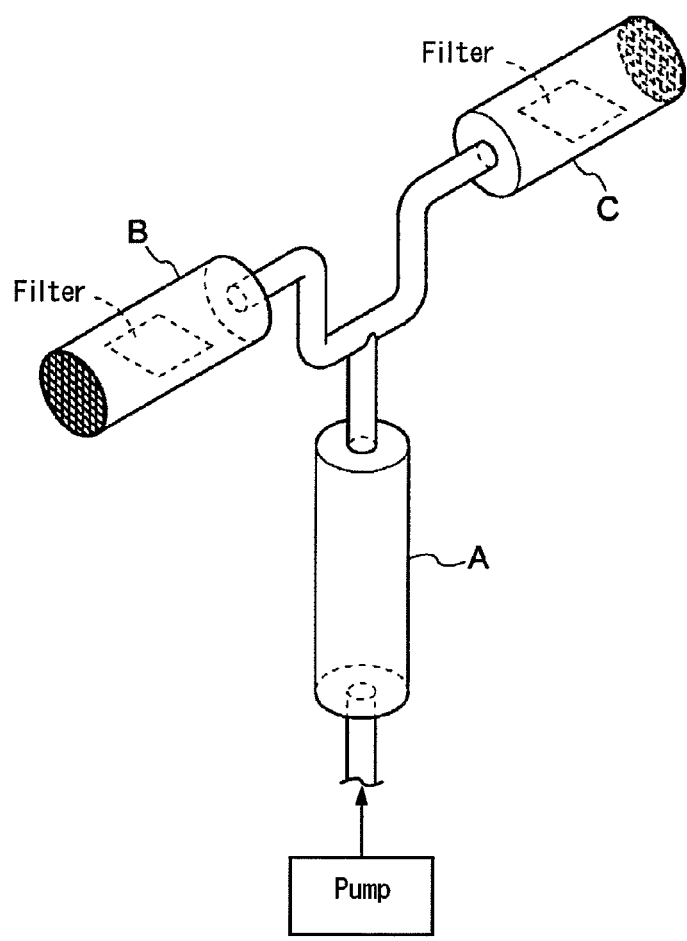

FLY ATTRACTANT COMPOSITION AND FLY ATTRACTING METHOD, AS WELL AS FLY EXPELLANT COMPOSITION AND FLY EXPELLING METHOD

BACKGROUND OF THE INVENTION

The present invention relates to a fly attractant composition and a fly attracting method, as well as a fly expellant composition and a fly expelling method.

Heretofore, a fly attractant composition comprising a combination of a pyrethroid compound as an insecticidal ingredient and a fly sex pheromone as an attractive ingredient has been known (see, for example, JP-B 5-60441).

SUMMARY OF THE INVENTION

An object of the present invention is to provide a fly attractant composition which has an excellent attracting effect on flies and a fly attracting method, as well as a fly expellant composition which has an excellent attracting and expelling effect on flies and a fly expelling method.

The present inventors intensively studied, and as a result, found that a ligninsulfonate had an excellent attracting effect on flies. Thus, the present invention was completed.

The present invention provides:

(1) A fly attractant composition containing a ligninsulfonate as an active ingredient;

(2) A fly expellant composition containing 5 to 20% by weight of a ligninsulfonate and at least 0.1% by weight but less than 5% by weight of an insecticidal active ingredient;

(3) The fly expellant composition according to the above (2), wherein the content of the ligninsulfonate is 4 to 200 times the content of the insecticidal active ingredient;

(4) The fly expellant composition according to the above (2), wherein the content of the ligninsulfonate is 4 to 50 times the content of the insecticidal active ingredient;

(5) The fly expellant composition according to the above (2), wherein the content of the ligninsulfonate is 10 to 50 times the content of the insecticidal active ingredient;

(6) The fly expellant composition according to the above (2), wherein the content of the ligninsulfonate is 10 to 40 times the content of the insecticidal active ingredient;

(7) The fly expellant composition according to any one of the above (2) to (6), wherein the insecticidal active ingredient is at least one compound selected from neonicotinoid compounds;

(8) The fly expellant composition according to any one of the above (2) to (6), wherein the insecticidal active ingredient is at least one compound selected from the group consisting of clothianidin, nitenpyram, imidacloprid, thiacloprid, acetamiprid and thiamethoxam;

(9) The fly expellant composition according to any one of the above (2) to (6), wherein the insecticidal active ingredient is clothianidin;

(10) The fly attractant composition or the fly expellant composition according to any one of the above (1) to (9), which further contains a fly sex pheromone;

(11) The fly expellant composition according to any one of the above (1) to (10), wherein the content of the fly sex pheromone is 0.05 to 1% by weight;

(12) The fly attractant composition or the fly expellant composition according to the above (10) or (11), wherein the fly sex pheromone is cis-9-tricosene;

(13) The fly attractant composition or fly expellant composition according to any one of the above (1) to (12), wherein the ligninsulfonate is sodium ligninsulfonate or calcium ligninsulfonate;

(14) The fly expellant composition according to any one of the above (2) to (13), which is in the form of a poison bait;

(15) A method of attracting a fly which comprises applying an effective amount of a ligninsulfonate to an area where the fly lives;

(16) A method of attracting a fly which comprises applying effective amounts of a ligninsulfonate and a fly sex pheromone to an area where the fly lives;

(17) A method of expelling a fly which comprises applying effective amounts of a ligninsulfonate and an insecticidal active ingredient to an area where the fly lives; and

(18) A method of expelling a fly which comprises applying effective amounts of a ligninsulfonate, a fly sex pheromone and an insecticidal active ingredient to an area where the fly lives.

BRIEF DESCRIPTION OF THE DRAWINGS

FIG. 1 shows a schematic view of a device used in Test Example 3.

DETAILED DESCRIPTION OF THE INVENTION

The fly attractant composition of the present invention contains a ligninsulfonate as an active ingredient.

Examples of the ligninsulfonate include sodium ligninsulfonate, calcium ligninsulfonate, magnesium ligninsulfonate, and ammonium ligninsulfonate.

As used herein, the ligninsulfonate also includes ligninsulfonate derivatives, and examples thereof include condensates of ligninsulfonates and formalin.

The fly attractant composition of the present invention can contain one or more compounds selected from the group consisting of ligninsulfonates and ligninsulfonate derivatives.

The ligninsulfonate is a known compound, and, for example, a commercially available ligninsulfonate can be used in the present invention.

Examples of commercially available ligninsulfonates include Reax85A (a product name of a sodium ligninsulfonate manufactured by MeadWestvaco Corporation), Reax83A (a product name of a sodium ligninsulfonate manufactured by MeadWestvaco Corporation), Reax910 (a product name of a condensate of sodium ligninsulfonate and formalin manufactured by MeadWestvaco Corporation), Ufoxane3A (a product name of a sodium ligninsulfonate manufactured by Borregaard), Ultrazine Na (a product name of a sodium ligninsulfonate manufactured by Borregaard), NEWKALGEN WG-4 (a product name of a sodium ligninsulfonate manufactured by TAKEMOTO OIL & FAT Co., Ltd.), NEWKALGEN RX-B (a product name of a sodium ligninsulfonate manufactured by TAKEMOTO OIL & FAT Co., Ltd.), VANILLEX RN (a product name of a sodium ligninsulfonate manufactured by NIPPON PAPER CHEMICALS CO., LTD.), VANILLEX N (a product name of a sodium ligninsulfonate manufactured by NIPPON PAPER CHEMICALS CO., LTD.), VANILLEX NP (a product name of an ammonium ligninsulfonate manufactured by NIPPON PAPER CHEMICALS CO., LTD.), SANX P201 (a product name of a calcium ligninsulfonate manufactured by NIPPON PAPER CHEMICALS CO., LTD.), SANX 252 (a product name of a sodium ligninsulfonate manufactured by NIPPON PAPER CHEMICALS CO., LTD.), SANX P252 (a product name of a sodium ligninsulfonate manufactured by NIPPON PAPER CHEMICALS CO., LTD.), Kraftsperse EDF-350 (a product name of a kraft sodium ligninsulfonate manufactured by MeadWestvaco Corporation), and Kraftsperse EDF-450 (a product name of a kraft sodium ligninsulfonate manufactured by MeadWestvaco Corporation).

The ligninsulfonate that is the active ingredient of the fly attractant composition of the present invention can exhibit a sufficient attracting effect on flies at a small amount.

The fly attractant composition of the present invention may be the ligninsulfonate itself or the ligninsulfonate formulated into various forms. When the fly attractant composition of the present invention is used in the form of a formulation, the amount of the ligninsulfonate contained in the fly attractant composition is not particularly limited and can be determined as appropriate. It is preferable that the fly attractant composition of the present invention contains usually 0.1 to 99.9% by weight, preferably 0.5 to 99.9% by weight of the ligninsulfonate.

The fly attractant composition of the present invention can further contain a fly sex pheromone. The "pheromone" means a species-specific aromatic chemical substance that is produced by an insect for the purpose of communication between the same species of insects, and there are various kinds of pheromones including sex pheromones and aggregation pheromones. Sex pheromones are used for communication between the sexes in mating behavior. An example of sex pheromones is an aromatic substance secreted from a sexually mature female in order to attract males for mating behavior. The fly attractant composition of the present invention can contain one or more kinds of fly sex pheromones.

Examples of the fly sex pheromone include 9-tricosene, cis-9-tricosene, 10-methyl-9-tricosene, cis-2-methyl-8-docosene, cis-9-docosene, cis-8-docosene and cis-10-tricosene. Preferred is cis-9-tricosene.

In the case where the fly attractant composition of the present invention contains a ligninsulfonate and a fly sex pheromone as the active ingredients, the fly attractant composition can be prepared by simply mixing the ligninsulfonate and the fly sex pheromone or by formulating a mixture of the ligninsulfonate and the fly sex pheromone into various forms. The content rates of the ligninsulfonate and the fly sex pheromone in the fly attractant composition of the present invention are not particularly limited and can be determined as appropriate. It is preferable that the fly attractant composition of the present invention contains usually 0.1 to 99.9% by weight, preferably 0.5 to 99.9% by weight of the ligninsulfonate and usually 0.001 to 1% by weight, preferably 0.005 to 0.5% by weight of the fly sex pheromone.

The fly expellant composition of the present invention contains a combination of a ligninsulfonate and an insecticidal active ingredient or contains a combination of a ligninsulfonate, a fly sex pheromone and an insecticidal active ingredient. Examples of the ligninsulfonate and the fly sex pheromone are the same as described above for the fly attractant composition of the present invention.

Examples of the insecticidal active ingredient include neonicotinoid compounds, organic phosphorus insecticides (e.g., dichlorvos, fenitrothion, azamethiphos, prothiofos, trichlorphon, etc.), carbamate insecticides (e.g., propoxur, etc.), phenylpyrazole insecticides (e.g., ethiprole, fipronil, pyriprole, etc.), benzoylurea insecticides (e.g., chlorflua-zuron, bistrifluoron, diflubenzuron, flufenoxuron, hexaflumuron, lufenuron, novaluron, noviflumuron, triflumuron, etc.), and other insecticides (e.g., avermectin, chlorphenapyr, cyromazine, hydroprene, methoprene, indoxacarb, metoxadiazone, pyridalyl, pyriproxyfen, spinosad, sulfluramid, flubendiamide, metaflumizone, spirotetramat, pyrifluquinazone, spinetoram, chlorantraniliprole, etc.). The fly expellant composition of the present invention can contain one or more kinds of insecticidal active ingredients.

Preferable examples of the insecticidal active ingredient to be contained in the fly expellant composition of the present invention include neonicotinoid compounds.

Preferable examples of the neonicotinoid compounds include clothianidin, nitenpyram, imidacloprid, thiacloprid, acetamiprid, thiamethoxam and dinotefuran.

Clothianidin can be produced, for example, according to a method described in JP-B 2546003.

Nitenpyram can be produced, for example, according to a method described in JP-B 2122839.

Imidacloprid can be produced, for example, according to a method described in JP-B 1880961.

Thiacloprid can be produced, for example, according to a method described in JP-B 1985059.

Acetamiprid can be produced, for example, according to a method described in JP-B 2926954.

Thiamethoxam can be produced, for example, according to a method described in JP-B 3487614.

Dinotefuran can be produced, for example, according to a method described in JP-B 2766848.

In the case where the fly expellant composition of the present invention contains neonicotinoid compounds, the composition can contain one or more kinds of neonicotinoid compounds.

The insecticidal active ingredient to be contained in the expellant composition of the present invention may have geometric isomers and/or stereoisomers. In the present invention, the insecticidal active ingredient includes each isomer alone and mixtures of isomers in any ratios.

The insecticidal active ingredient may be in the form of an agrochemically acceptable salt with an acid or a base.

Examples of the acid include inorganic acids such as hydrochloric acid, hydrobromic acid, hydroiodic acid, phosphoric acid, sulfuric acid and perchloric acid, and organic acids such as formic acid, acetic acid, tartaric acid, malic acid, citric acid, oxalic acid, succinic acid, benzoic acid, picric acid, methanesulfonic acid and p-toluenesulfonic acid.

Examples of the base include alkaline metals such as sodium, potassium and lithium, alkaline earth metal such as calcium and magnesium, inorganic bases such as ammonia, and organic bases such as pyridine, collidine, triethylamine and triethanolamine.

In the present invention, the insecticidal active ingredient includes agrochemically acceptable salts of the above-described insecticidal active ingredients formed with the above-described acids or bases.

In the case where the fly expellant composition of the present invention contains a ligninsulfonate and an insecticidal active ingredient as the active ingredients, the fly expellant composition can be prepared by simply mixing the ligninsulfonate and the insecticidal active ingredient or by formulating a mixture of the ligninsulfonate and the insecticidal active ingredient into various forms. The content rates of the ligninsulfonate and the insecticidal active ingredient in the fly expellant composition of the present invention are not particularly limited and can be determined as appropriate. It is preferable that the fly expellant composition of the present invention contains usually 0.4 to 99.9% by weight, preferably 5 to 20% by weight of the ligninsulfonate and usually at least 0.1% by weight but less than 5% by weight of the insecticidal active ingredient. It is more preferable that the content of the ligninsulfonate in the fly expellant composition is 4 to 200 times, preferably 5 to 50 times, more preferably 10 to 50 times, still more preferably 10 to 40 times the content of the insecticidal active ingredient in the fly expellant composition.

In the case where the fly expellant composition of the present invention contains a ligninsulfonate, a fly sex pheromone and an insecticidal active ingredient as the active ingredients, the fly expellant composition can be prepared by simply mixing the ligninsulfonate, the fly sex pheromone and the insecticidal active ingredient or by formulating a mixture of the ligninsulfonate, the fly sex pheromone and the insecticidal active ingredient into various forms. The content rates of the ligninsulfonate, the fly sex pheromone and the insecticidal active ingredient in the fly expellant composition of the present invention are not particularly limited and can be determined as appropriate. It is preferable that the fly expellant composition of the present invention contains usually 0.4 to 99.8% by weight, preferably 5 to 20% by weight of the ligninsulfonate, usually 0.001 to 1% by weight, preferably 0.05 to 1% by weight of the fly sex pheromone and usually at least 0.1% by weight but less than 5% by weight of the insecticidal active ingredient. It is more preferable that the content of the ligninsulfonate in the fly expellant composition is 4 to 200 times, preferably 5 to 50 times, more preferably 10 to 50 times, still more preferably 10 to 40 times the content of the insecticidal active ingredient in the fly expellant composition.

When the fly attractant composition or the fly expellant composition of the present invention is used in the form of a formulation, the formulation may be a known form. Examples of the formulation include a liquid formulation, an emulsifiable concentrate, a wettable powder, a water dispersible granule, a water soluble powder, a sol formulation, a gel formulation, a paste formulation, a jelly formulation, a granule and a dust. In the case of the fly expellant composition, it can be also formulated into a poison bait. The formulation can be prepared by a known method.

The fly attractant composition or the fly expellant composition of the present invention can further contain other active ingredients such as bactericides (e.g., copper bactericides, organic chlorine bactericides, organic sulfur bactericides, phenol bactericides, benzimidazole bactericides, EBI (ergosterol biosynthesis inhibitor) bactericides, melanin biosynthesis inhibitor bactericides, acrylate bactericides, etc.) and fungicides; and additives as appropriate, as long as they do not deteriorate the attracting activity or expelling activity of the fly attractant composition or the fly expellant composition of the present invention. Examples of additives include antioxidants; ultraviolet protective agents; surfactants (e.g., nonionic and anionic surfactants such as polyoxyethylene alkylaryl ethers, polyethylene glycol ethers, polyhydric alcohol esters; alkyl sulfates, alkylbenzenesulfonates, dioctylsulfosuccinates, polycarboxylates, alpha-olefin sulfonates, etc.); preservatives; colorants (e.g., Yellow No. 4, Red No. 104, etc.); flavors (e.g., cheese flavor, chocolate flavor, etc.); accidental ingestion prevention agents (e.g., denatonium benzoate, etc.); pH regulators (e.g., citric acid, phosphate buffer, sodium bicarbonate, etc.); liquid carriers such as water, alcohols (e.g., methyl alcohol, ethyl alcohol, isopropyl alcohol, ethylene glycol, etc.), ketones (e.g., acetone, methyl ethyl ketone, etc.), ethers (e.g., dioxane, tetrahydrofuran, ethylene glycol monomethyl ether, diethylene glycol monomethyl ether, propylene glycol monomethyl ether, etc.), fatty acid hydrocarbons (e.g., hexane, kerosine, heating oil, paraffin, etc.), aromatic hydrocarbons (e.g., benzene, toluene, xylene, methylnaphthalene, etc.), halogenated hydrocarbons (e.g., dichloromethane, chloroform, carbon tetrachloride, etc.), acid amides (e.g., N,N-dimethylformamide, N,N-dimethylacetamide, etc.), esters (e.g., ethyl acetate, butyl acetate, fatty acid glycerin ester, etc.), and nitriles (e.g., acetonitrile, propionitrile, etc.); and solid carriers such as plant powder (e.g., soybean powder, tobacco powder, wheat flour, wood powder, sugars, etc.), mineral powder (e.g., clays such as white carbon, kaolin, bentonite, and acidic white clay, talc such as talcum powder and agalmatolite, diatomaceous earth, silica such as mica powder, etc.), alumina, sulfur powder, and active carbon.

Further, for the purpose of enhancing attracting activity on flies, the fly attractant composition or the fly expellant composition of the present invention may be used in combination with various attractive agents (e.g., honey, sugar, liquid sugar, milk, powdered skim milk, rice bran, bran, corn flour, wheat flour, chicken egg, feed ingredients such as animal feed, aromatic ingredients such as anethole, linalool and carvone, vinegar, acetoin, furfural, etc.).

The amount of the other active ingredients (e.g., bactericides or fungicides) contained in the fly attractant composition or fly expellant composition of the present invention is usually 0.1 to 99.799% by weight, preferably 1 to 20% by weight of the entire composition. The amount of the additives contained in the fly attractant composition or fly expellant composition of the present invention is usually 0.1 to 99.799% by weight, preferably 1 to 99% by weight of the entire composition, depending on the kind or content of the active ingredient of the fly attractant composition or fly expellant composition. Specifically, for example, when the fly attractant composition or fly expellant composition of the present invention is a liquid formulation, it is preferable that the fly attractant composition or fly expellant composition contains usually 1 to 20% by weight, preferably 1 to 10% by weight of a surfactant and 20 to 80% by weight of water. When the fly attractant composition or fly expellant composition of the present invention is an emulsifiable concentrate or a wettable powder (e.g., a water dispersible granule), the fly attractant composition or fly expellant composition is preferably diluted with water or the like (e.g., about 2 to 100-fold dilution) before use.

Examples of flies against which the fly attractant composition or fly expellant composition of the present invention exhibits an attracting effect or an attracting and expelling effect include flies living in or coming to a livestock shed or a chicken shed. Specific examples thereof include flies belonging to Muscidae such as *Musca domestica, Fannia canicularis, Muscina stabulans*, and *Stomoxys calcitrans*; Calliphoridae such as *Calliphora lata, Calliphora vicina, Aldrichina grahami*, and *Lucilia illustris*; and Sarcophagidae such as *Boettcherisca peregrina*.

According to the attracting method of the present invention, a fly can be attracted by applying an effective amount of a ligninsulfonate or effective amounts of a ligninsulfonate and a fly sex pheromone to an area where the fly lives.

According to the expelling method of the present invention, a fly can be attracted and expelled by applying effective amounts of a ligninsulfonate and an insecticidal active ingredient or effective amounts of a ligninsulfonate, a fly sex pheromone and an insecticidal active ingredient to an area where the fly lives.

Examples of the area where a fly lives include a livestock shed and a chicken shed, and specifically, a cattle shed, a pigsty, and a chicken farm, as well as places for rearing other livestock and pets (e.g., horse, sheep, goat, camel, buffalo, donkey, rabbit, deer, reindeer, mink, dog, cat, etc.), and poultry (e.g., duck, turkey, quail, etc.). Examples of the area where a fly lives as used herein also include indoor or outdoor places near a livestock shed, a chicken shed or the like where excretion, refuse and spilled feed are collected and accumulated from the shed.

When a ligninsulfonate and a fly sex pheromone, a ligninsulfonate and an insecticidal active ingredient, or a ligninsulfonate, a fly sex pheromone and an insecticidal active ingredient are applied to an area where a fly lives, although they may be applied as discrete formulations at the same time, they are usually applied as the fly attractant composition or fly expellant composition of the present invention in view of ease.

Usually, in the attracting method or expelling method of the present invention, the fly attractant composition or fly expellant composition of the present invention is applied.

Examples of the application method include spraying on an area where a fly lives, coating of an area where a fly lives, and installation in an area where a fly lives.

Spraying on an area where a fly lives is performed, for example, by spraying the fly attractant composition or fly expellant composition of the present invention on an area where a fly comes to. Preferable examples of formulations used for spraying include a water soluble powder, a liquid formulation, a wettable powder, a water dispersible granule, a dust, and an emulsifiable concentrate. The application amount may be varied depending on, for example, the application period, the application place, and the application method. The application amount is usually from 0.001 to 100 $g/m^2$, preferably 0.1 to 20 $g/m^2$ in terms of the total amount of the attractive ingredients or the attractive and expellant ingredients. A liquid formulation is applied as it is. A solid formulation is applied after dilution with water.

Coating of an area where a fly lives is performed, for example, by coating the wall, door, pillar, window, floor, ceiling or joist of a livestock shed or a chicken shed with the fly attractant composition or fly expellant composition of the present invention. In the case of coating, the application amount is usually from 0.001 to 100 $g/m^2$, preferably 0.1 to 20 $g/m^2$ in terms of the total amount of the attractive ingredients or the attractive and expellant ingredients.

Installation in an area where a fly lives is performed, for example, by putting the fly attractant composition or fly expellant composition of the present invention in a container and then standing or suspending the container, by treating a plate (e.g., having size of 10 cm×20 cm to 1 m×2 m) with the fly attractant composition or fly expellant composition of the present invention and then standing or suspending the plate, or by diluting the fly expellant composition of the present invention with water or the like to prepare a poison bait, putting the poison bait in a tray (e.g., having size of 10 cm×10 cm to 1 m×2 m) and then placing the tray in an area where a fly lives. Installation in an area where a fly lives can be also performed by putting the fly attractant composition or fly expellant composition of the present invention in a trap having a means to catch flies and then installing the trap in an area where a fly lives. Examples of the trap include a container capable of holding a fly attractant composition inside or the like and having an opening form which its attractive ingredient is released, whereby once flies entered the container from the opening, the flies can not escape out of the container, and a sheet, a plate and a rope which are provided with adhesive property together with an attractive ingredient of a fly attractant composition or the like. In addition, for example, an appropriate amount (50 ml to 500 ml) of a poison bait is put in a PET bottle whose side is bored and the PET bottle can be used as a simple trap.

The fly attractant composition of the present invention has an excellent attracting effect on flies. The fly expellant composition of the present invention has an excellent attracting and expelling effect on flies.

EXAMPLES

Hereinafter, the present invention will be described in more detail by way of Formulation Examples and Test Examples. However, the present invention is not limited thereto.

Formulation Example 1

In 97% by weight of water, 3% by weight of Reax910 (a product name of a condensate of sodium ligninsulfonate and formalin manufactured by MeadWestvaco Corporation) is dissolved to obtain a formulation 1.

Then, 2 g of the formulation 1 is put in a plastic container (diameter: 9 cm; height: 5 cm) with a lid having a hole (1.5 cm×1.5 cm) from which flies can enter the container, to obtain a device for catching flies.

Formulation Example 2

In a mortar, 90% by weight of Reax910 (a product name of a condensate of sodium ligninsulfonate and formalin manufactured by MeadWestvaco Corporation) and 10% by weight of Fubasami clay A-300 (a product name of agalmatolite clay manufactured by Fubasami Clay Co., Ltd.) are mixed to obtain a formulation 2.

Then, 2 g of the formulation 2 is put in a plastic container (diameter: 9 cm; height: 5 cm) with a lid having a hole (1.5 cm×1.5 cm) from which flies can enter the container, to obtain a device for catching flies.

Formulation Example 3

In a mortar, 3% by weight of Reax910 (a product name of a condensate of sodium ligninsulfonate and formalin manufactured by MeadWestvaco Corporation), 0.05% by weight of cis-9-tricosene (Wako Pure Chemical Industries, Ltd.) and 96.95% by weight of Fubasami clay A-300 (a product name of agalmatolite clay manufactured by Fubasami Clay Co., Ltd.) are mixed thoroughly to obtain a formulation 3.

Then, 2 g of the formulation 3 is put in a plastic container (diameter: 9 cm; height: 5 cm) with a lid having a hole (1.5 cm×1.5 cm) from which flies can enter the container, to obtain a device for catching flies.

Formulation Example 4

In a mortar, 20 parts by weight of Reax910 (a product name of a condensate of sodium ligninsulfonate and formalin manufactured by MeadWestvaco Corporation) and 0.1 part by weight of cis-9-tricosene (Wako Pure Chemical Industries, Ltd.) are mixed thoroughly to obtain a formulation 4.

Then, 2 g of the formulation 4 is put in a plastic container (diameter: 9 cm; height: 5 cm) with a lid having a hole (1.5 cm×1.5 cm) from which flies can enter the container, to obtain a device for catching flies.

Formulation Example 5

In 97% by weight of water, 3% by weight of VANILLEX N (a product name of a sodium ligninsulfonate manufactured by NIPPON PAPER CHEMICALS CO., LTD.) is dissolved to obtain a formulation 5.

Then, 2 g of the formulation 5 is put in a plastic container (diameter: 9 cm; height: 5 cm) with a lid having a hole (1.5 cm×1.5 cm) from which flies can enter the container, to obtain a device for catching flies.

Formulation Example 6

In a mortar, 90% by weight of VANILLEX N (a product name of a sodium ligninsulfonate manufactured by NIPPON PAPER CHEMICALS CO., LTD.) and 10% by weight of Fubasami clay A-300 (a product name of agalmatolite clay manufactured by Fubasami Clay Co., Ltd.) are mixed to obtain a formulation 6.

Then, 2 g of the formulation 6 is put in a plastic container (diameter: 9 cm; height: 5 cm) with a lid having a hole (1.5 cm×1.5 cm) from which flies can enter the container, to obtain a device for catching flies.

Formulation Example 7

In a mortar, 3% by weight of VANILLEX N (a product name of a sodium ligninsulfonate manufactured by NIPPON PAPER CHEMICALS CO., LTD.), 0.05% by weight of cis-9-tricosene (Wako Pure Chemical Industries, Ltd.) and 96.95% by weight of Fubasami clay A-300 (a product name of agalmatolite clay manufactured by Fubasami Clay Co., Ltd.) are mixed thoroughly to obtain a formulation 7.

Then, 2 g of the formulation 7 is put in a plastic container (diameter: 9 cm; height: 5 cm) with a lid having a hole (1.5 cm×1.5 cm) from which flies can enter the container, to obtain a device for catching flies.

Formulation Example 8

In a mortar, 20 parts by weight of VANILLEX N (a product name of a sodium ligninsulfonate manufactured by NIPPON PAPER CHEMICALS CO., LTD.) and 0.1 part by weight of cis-9-tricosene (Wako Pure Chemical Industries, Ltd.) are mixed thoroughly to obtain a formulation 8.

Then, 2 g of the formulation 8 is put in a plastic container (diameter: 9 cm; height: 5 cm) with a lid having a hole (1.5 cm×1.5 cm) from which flies can enter the container, to obtain a device for catching flies.

Formulation Example 9

In a mortar, 5% by weight of clothianidin, 3% by weight (0.6 times the amount of clothianidin) of Reax910 (a product name of a condensate of sodium ligninsulfonate and formalin manufactured by MeadWestvaco Corporation), and 92% by weight of lactose were mixed thoroughly. To the mixture was added an appropriate amount of water and then kneaded. The kneaded mixture was pressed into a perforated plate having multiple holes 3.0 mm in diameter with fingers to obtain cylindrical granules. The granule was dried to obtain a formulation 9.

Formulation Example 10

In a mortar, 5% by weight of clothianidin, 3% by weight (0.6 times the amount of clothianidin) of NEWKALGEN WG-4 (a product name of a sodium ligninsulfonate manufactured by TAKEMOTO OIL & FAT Co., Ltd.), and 92% by weight of lactose were mixed thoroughly. To the mixture was added an appropriate amount of water and then kneaded. The kneaded mixture was pressed into a perforated plate having multiple holes 3.0 mm in diameter with fingers to obtain cylindrical granules. The granule was dried to obtain a formulation 10.

Formulation Example 11

In a mortar, 1% by weight of clothianidin, 3% by weight of SORPOL 5515 (a product name of alpha-olefin sulfonic acid manufactured by TOHO Chemical Industry Co., Ltd.), 5% by weight (5 times the amount of clothianidin) of Reax910 (a product name of a condensate of sodium ligninsulfonate and formalin manufactured by MeadWestvaco Corporation), and 91% by weight of sucrose were mixed thoroughly. To the mixture was added an appropriate amount of water and then kneaded. The kneaded mixture was pressed into a perforated plate having multiple holes 1.0 mm in diameter with fingers to obtain cylindrical granules. The granule was dried to obtain a formulation 11.

Formulation Example 12

In a mortar, 0.5% by weight of clothianidin, 1% by weight of EMAL 10PT (a product name of sodium lauryl sulfate manufactured by Kao Corporation), 10% by weight (20 times the amount of clothianidin) of Reax910 (a product name of a condensate of sodium ligninsulfonate and formalin manufactured by MeadWestvaco Corporation), 0.1% by weight of cis-9-tricosene (Wako Pure Chemical Industries, Ltd.), 20% by weight of Fubasami clay A-300 (a product name of agalmatolite clay manufactured by Fubasami Clay Co., Ltd.), and 68.4% by weight of sucrose were mixed thoroughly. To the mixture was added an appropriate amount of water and then kneaded. The kneaded mixture was pressed into a perforated plate having multiple holes 1.5 mm in diameter with fingers to obtain cylindrical granules. The granule was dried to obtain a formulation 12.

Formulation Example 13

In a mortar, 0.5% by weight of clothianidin, 1% by weight of EMAL 10PT (a product name of sodium lauryl sulfate manufactured by Kao Corporation), 20% by weight (40 times the amount of clothianidin) of Reax910 (a product name of a condensate of sodium ligninsulfonate and formalin manufactured by MeadWestvaco Corporation), 0.1% by weight of cis-9-tricosene (Wako Pure Chemical Industries, Ltd.), 3% by weight of CARPLEX #80D (a product name of white carbon manufactured by Shionogi & Co., Ltd.), 10% by weight of Bentonite FUJI (a product name of bentonite manufactured by HOJUN), and 65.4% by weight of sucrose were mixed thoroughly. To the mixture was added an appropriate amount of water and then kneaded. The kneaded mixture was pressed into a perforated plate having multiple holes 0.7 mm in diameter with fingers to obtain cylindrical granules. The granule was dried to obtain a formulation 13.

Formulation Example 14

In a mortar, 0.5% by weight of clothianidin, 1% by weight of EMAL 10PT (a product name of sodium lauryl sulfate manufactured by Kao Corporation), 10% by weight (20 times the amount of clothianidin) of VANILLEX N (a product name of a sodium ligninsulfonate manufactured by NIPPON PAPER CHEMICALS CO., LTD.), 0.1% by weight of cis-9-tricosene (Wako Pure Chemical Industries, Ltd.), 20% by weight of Fubasami clay A-300 (a product name of agalmatolite clay manufactured by Fubasami Clay Co., Ltd.), and 68.4% by weight of sucrose are mixed thoroughly. To the mixture is added an appropriate amount of water and then kneaded. The kneaded mixture is pressed into a perforated plate having multiple holes 1.5 mm in diameter with fingers to obtain cylindrical granules. The granule is dried to obtain a formulation 14.

Formulation Example 15

In a mortar, 0.5% by weight of clothianidin, 1% by weight of EMAL 10PT (a product name of sodium lauryl sulfate manufactured by Kao Corporation), 20% by weight (40 times the amount of clothianidin) of VANILLEX N (a product name of a sodium ligninsulfonate manufactured by NIPPON PAPER CHEMICALS CO., LTD.), 0.1% by weight of cis-9-tricosene (Wako Pure Chemical Industries, Ltd.), 3% by weight of CARPLEX #80D (a product name of white carbon manufactured by Shionogi & Co., Ltd.), 10% by weight of Bentonite FUJI (a product name of bentonite manufactured by HOJUN), and 65.4% by weight of sucrose are mixed thoroughly. To the mixture is added an appropriate amount of water and then kneaded. The kneaded mixture is pressed into a perforated plate having multiple holes 0.7 mm in diameter with fingers to obtain cylindrical granules. The granule is dried to obtain a formulation 14.

Formulation Example 16

In a mortar, 0.5% by weight of imidacloprid, 1% by weight of EMAL 10PT (a product name of sodium lauryl sulfate manufactured by Kao Corporation), 10% by weight (20 times the amount of imidacloprid) of Reax910 (a product name of a condensate of sodium ligninsulfonate and formalin manufactured by MeadWestvaco Corporation), 0.1% by weight of cis-9-tricosene (Wako Pure Chemical Industries, Ltd.), 20% by weight of Fubasami clay A-300 (a product name of agalmatolite clay manufactured by Fubasami Clay Co., Ltd.), and 68.4% by weight of sucrose are mixed thoroughly. To the mixture is added an appropriate amount of water and then kneaded. The kneaded mixture is pressed into a perforated plate having multiple holes 1.5 mm in diameter with fingers to obtain cylindrical granules. The granule is dried to obtain a formulation 16.

Formulation Example 17

In a mortar, 0.5% by weight of imidacloprid, 1% by weight of EMAL 10PT (a product name of sodium lauryl sulfate manufactured by Kao Corporation), 20% by weight (40 times the amount of imidacloprid) of Reax910 (a product name of a condensate of sodium ligninsulfonate and formalin manufactured by MeadWestvaco Corporation), 0.1% by weight of cis-9-tricosene (Wako Pure Chemical Industries, Ltd.), 3% by weight of CARPLEX #80D (a product name of white carbon manufactured by Shionogi & Co., Ltd.), 10% by weight of Bentonite FUJI (a product name of bentonite manufactured by HOJUN), and 65.4% by weight of sucrose are mixed thoroughly. To the mixture is added an appropriate amount of water and then kneaded. The kneaded mixture is pressed into a perforated plate having multiple holes 0.7 mm in diameter with fingers to obtain cylindrical granules. The granule is dried to obtain a formulation 17.

Formulation Example 18

In a mortar, 0.5% by weight of imidacloprid, 1% by weight of EMAL 10PT (a product name of sodium lauryl sulfate manufactured by Kao Corporation), 10% by weight (20 times the amount of imidacloprid) of VANILLEX N (a product name of a sodium ligninsulfonate manufactured by NIPPON PAPER CHEMICALS CO., LTD.), 0.1% by weight of cis-9-tricosene (Wako Pure Chemical Industries, Ltd.), 20% by weight of Fubasami clay A-300 (a product name of agalmatolite clay manufactured by Fubasami Clay Co., Ltd.), and 68.4% by weight of sucrose are mixed thoroughly. To the mixture is added an appropriate amount of water and then kneaded. The kneaded mixture is pressed into a perforated plate having multiple holes 1.5 mm in diameter with fingers to obtain cylindrical granules. The granule is dried to obtain a formulation 18.

Formulation Example 19

In a mortar, 0.5% by weight of imidacloprid, 1% by weight of EMAL 10PT (a product name of sodium lauryl sulfate manufactured by Kao Corporation), 20% by weight (40 times the amount of imidacloprid) of VANILLEX N (a product name of a sodium ligninsulfonate manufactured by NIPPON PAPER CHEMICALS CO., LTD.), 0.1% by weight of cis-9-tricosene (Wako Pure Chemical Industries, Ltd.), 3% by weight of CARPLEX #80D (a product name of white carbon manufactured by Shionogi & Co., Ltd.), 10% by weight of Bentonite FUJI (a product name of bentonite manufactured by HOJUN), and 65.4% by weight of sucrose are mixed thoroughly. To the mixture is added an appropriate amount of water and then kneaded. The kneaded mixture is pressed into a perforated plate having multiple holes 0.7 mm in diameter with fingers to obtain cylindrical granules. The granule is dried to obtain a formulation 19.

Test Example 1

Each of the formulations 9 to 13 (each 20 g) was put in a separate tray (250 mm×600 mm). The trays were installed in a chicken shed. After 1.5 hours, the number of flies (*Musca domestica*) in the tray was counted, and an attracting effect was assessed.

Results are shown in Table 1.

TABLE 1

|  | Formulation 9 | Formulation 10 | Formulation 11 | Formulation 12 | Formulation 13 |
|---|---|---|---|---|---|
| Number of attracted flies | 41 | 32 | 83 | 75 | 82 |

Test Example 2

Each of the formulations 11, 12 and 13 (each 27 g) was diluted with 22 g of tap water. The total amount of each dilution thus obtained was applied to the surface of separate plywood (450 mm×900 mm). The plywood was installed in a chicken shed and a tray was placed under the plywood. After 1.5 hours, the number of flies (*Musca domestica*)

settling on the plywood and the number of knocked down flies (*Musca domestica*) in the tray were counted. An attracting effect was assessed from the sum of the counted numbers.

Results are shown in Table 2.

TABLE 2

Flies attracted on the surface of plywood and in a tray

|  | Formulation 11 | Formulation 12 | Formulation 13 |
|---|---|---|---|
| Total number of attracted flies | 113 | 151 | 144 |

Test Example 3

In a device shown in FIG. 1, flies (*Musca domestica*) were put in A (the ratio of numbers of male and female flies was male:female=1:1). Filters (3 cm×3 cm) were installed in B and C. Then, 120 mg of Reax910 (a product name of a condensate of sodium ligninsulfonate and formalin manufactured by MeadWestvaco Corporation) was diluted with 1 mL of water, and 0.05 mL of the dilution thus obtained was applied to the filter in B. The filter in C was not treated with any chemical. A pump was used to allow a flow of air through the device. After a given period of time, the number of the flies that moved from A to B or C was counted, and an attracting effect was assessed.

A test was repeated in the same manner as described above except that an untreated filter was installed in B and a filter treated with Reax910 was installed in C.

A result is shown in Table 3.

TABLE 3

| Test compound | Attracting rate (%) |
|---|---|
| Reax910 | 68.1 |

According to the present invention, a fly attractant composition which has a high attracting effect on flies and a method of effectively attracting flies, as well as a fly expellant composition which has a high attracting and expelling effect on flies and a method of effectively attracting and expelling flies can be provided.

What is claimed is:

1. A method of attracting a fly which comprises applying an effective amount of a ligninsulfonate to an area where the fly lives,
   wherein the ligninsulfonate is contained in a fly attractant composition, and the fly attractant composition contains 5 to 20% by weight of the ligninsulfonate and at least 0.1% by weight but less than 5% by weight of an insecticidal active ingredient, wherein the insecticidal active ingredient is at least one compound selected from the group consisting of clothianidin, nitenpyram, imidacloprid, thiacloprid, acetamiprid and thiamethoxam, wherein the content of the ligninsulfonate is 4 to 40.

2. A method of attracting a fly which comprises applying effective amount of a ligninsulfonate and a fly sex pheromone to an area where the fly lives, wherein the ligninsulfonate and the fly sex pheromone are contained in a fly attractant composition, and the fly attractant composition contains 5 to 20% by weight of the ligninsulfonate and at least 0.1% by weight but less than 5% by weight of an insecticidal active ingredient, wherein the insecticidal active ingredient is at least one compound selected from the group consisting of clothianidin, nitenpyram, imidacloprid, thiacloprid, acetamiprid and thiamethoxam, wherein the content of the ligninsulfonate is 4 to 40 times the content of the insecticidal active ingredient.

3. The method according to claim 1, wherein the content of the ligninsulfonate is 10 to 40 times the content of the insecticidal active ingredient.

4. The method according to claim 2, wherein the content of the ligninsulfonate is 10 to 40 times the content of the insecticidal active ingredient.

* * * * *